United States Patent [19]

Marin et al.

[11] Patent Number: 5,387,418
[45] Date of Patent: Feb. 7, 1995

[54] **METHOD FOR REPELLING *AEDES AEGYPTAE* USING OXY-SUBSTITUTED CARBOCYCLIC COMPOUNDS**

[75] Inventors: Anna B. Marin, Long Branch; Craig B. Warren, Rumson, both of N.J.; Jerry F. Butler, Gainesville, Fla.

[73] Assignees: International Flavors & Fragrances Inc., New York, N.Y.; The University of Florida, Gainesville, Fla.

[21] Appl. No.: 214,184

[22] Filed: Mar. 17, 1994

[51] Int. Cl.$^6$ .................. A01N 25/08; A01N 31/06
[52] U.S. Cl. .................. 424/409; 424/405; 424/DIG. 10; 514/919
[58] Field of Search .............. 424/405, 409, 411; 514/919, 470

[56] References Cited

U.S. PATENT DOCUMENTS 4,663,346  5/1987  Coulston .................. 514/456
5,165,926 11/1992  Wilson .................. 424/84

OTHER PUBLICATIONS

King, "Chemicals Evaluated As Insecticides and Repellents At Orlando, Fla." Agriculture Handbook No. 69, issued May 1954 (Entomology Research Service, Agricultural Research Service, U.S. Dept. of Agriculture; pp. 3, 13, 14, 15, 121, 122, 137 and 138 made of record).
Beroza, (I), "Materials Evaluated As Insecticides, Repellents And Chemosterilants At Orlando And Gainesville, Fla.", 1952–1964, Agriculture Handbook No. 340, issued Aug. 1967 (Agricultural Research Service, U.S. Dept. of Agriculture; pp. 110 and 120 made of record).
Beroza, (II), "Materials Tested As Insect Attractants", Agriculture Handbook No. 239, issued Jun. 1963, (Agricultural Research Service, U.S. Dept. of Agriculture, pp. 70 and 71 made of record).

*Primary Examiner*—Thurman K. Page
*Assistant Examiner*—Neil Levy
*Attorney, Agent, or Firm*—Arthur L. Liberman

[57] ABSTRACT

Described is a method for repelling *Aedes aegyptae* comprising exposing a three dimensional space inhabited by *Aedes aegyptae* to an *Aedes aegyptae*-repelling effective concentration and quantity of TONKA LACTONE ™ and insect repelling devices containing such compounds.

5 Claims, 8 Drawing Sheets

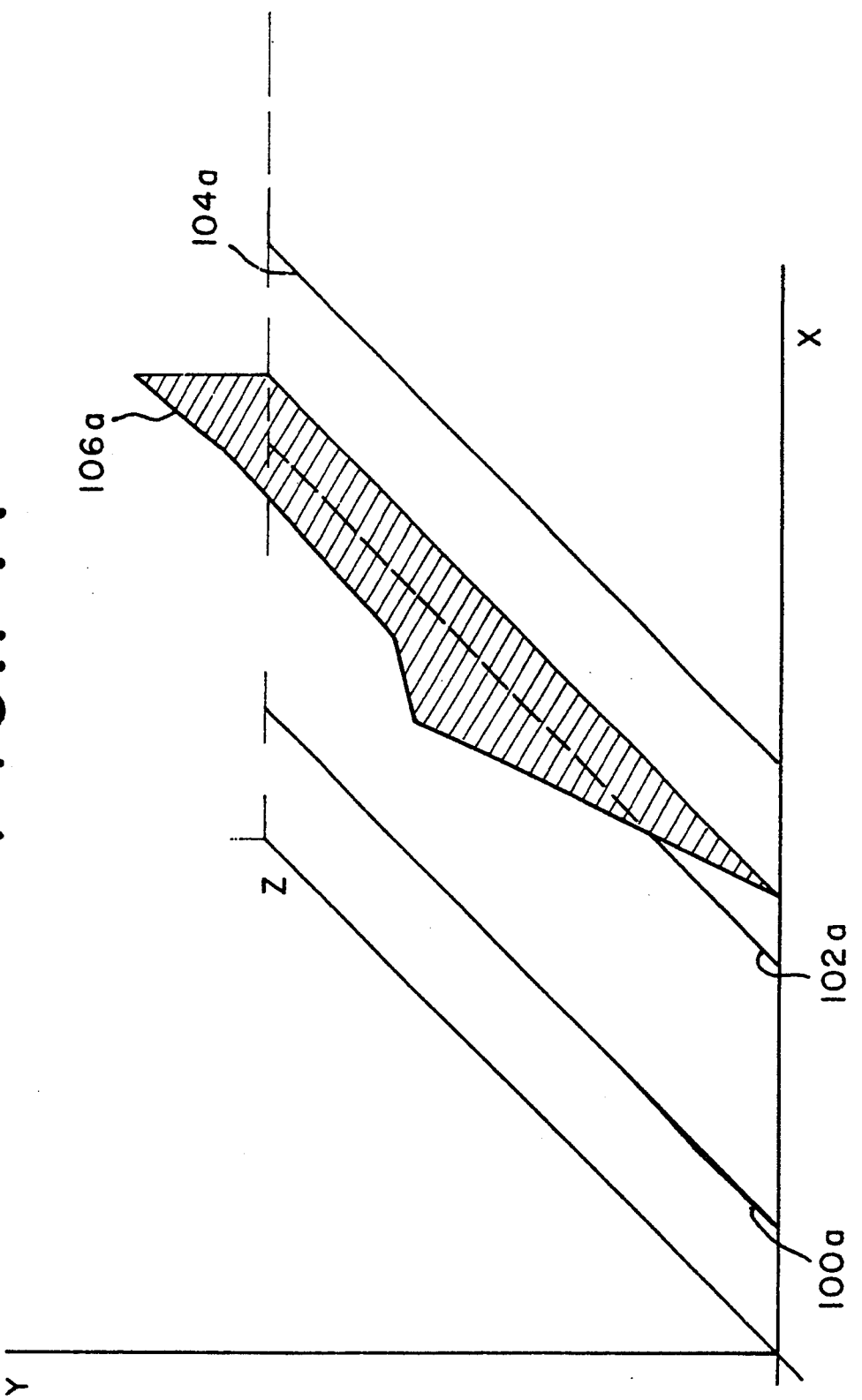

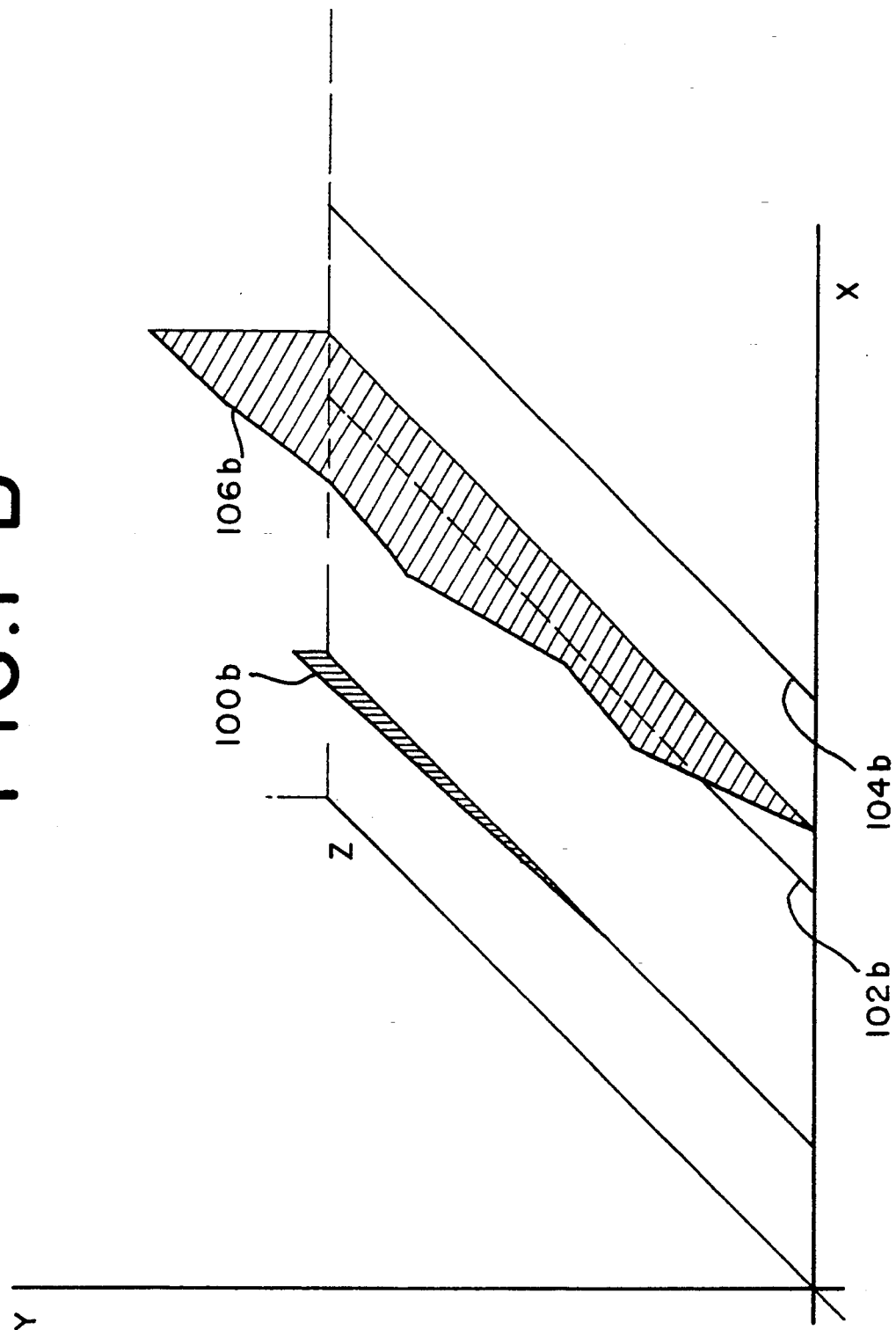

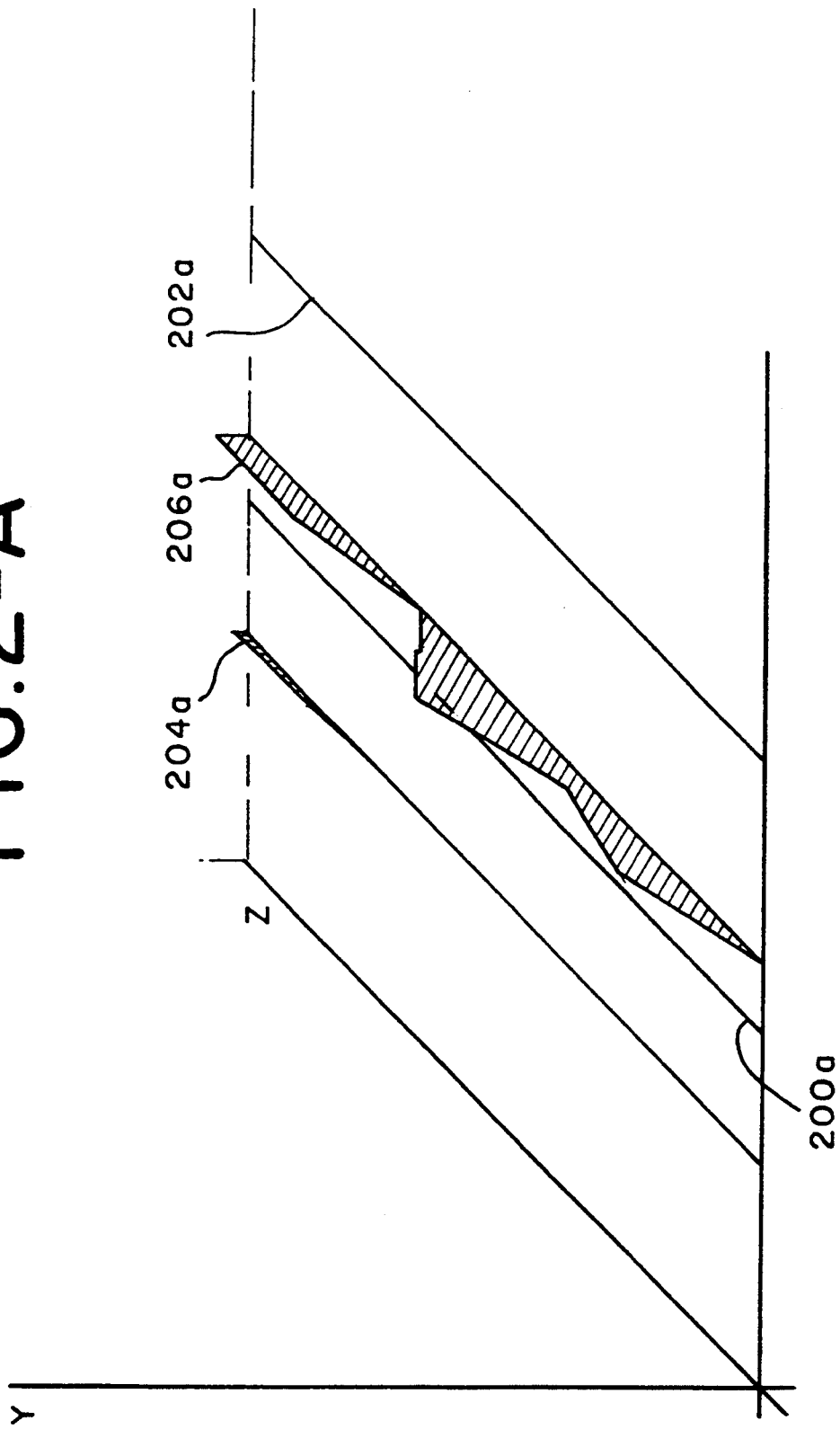
FIG.2-A

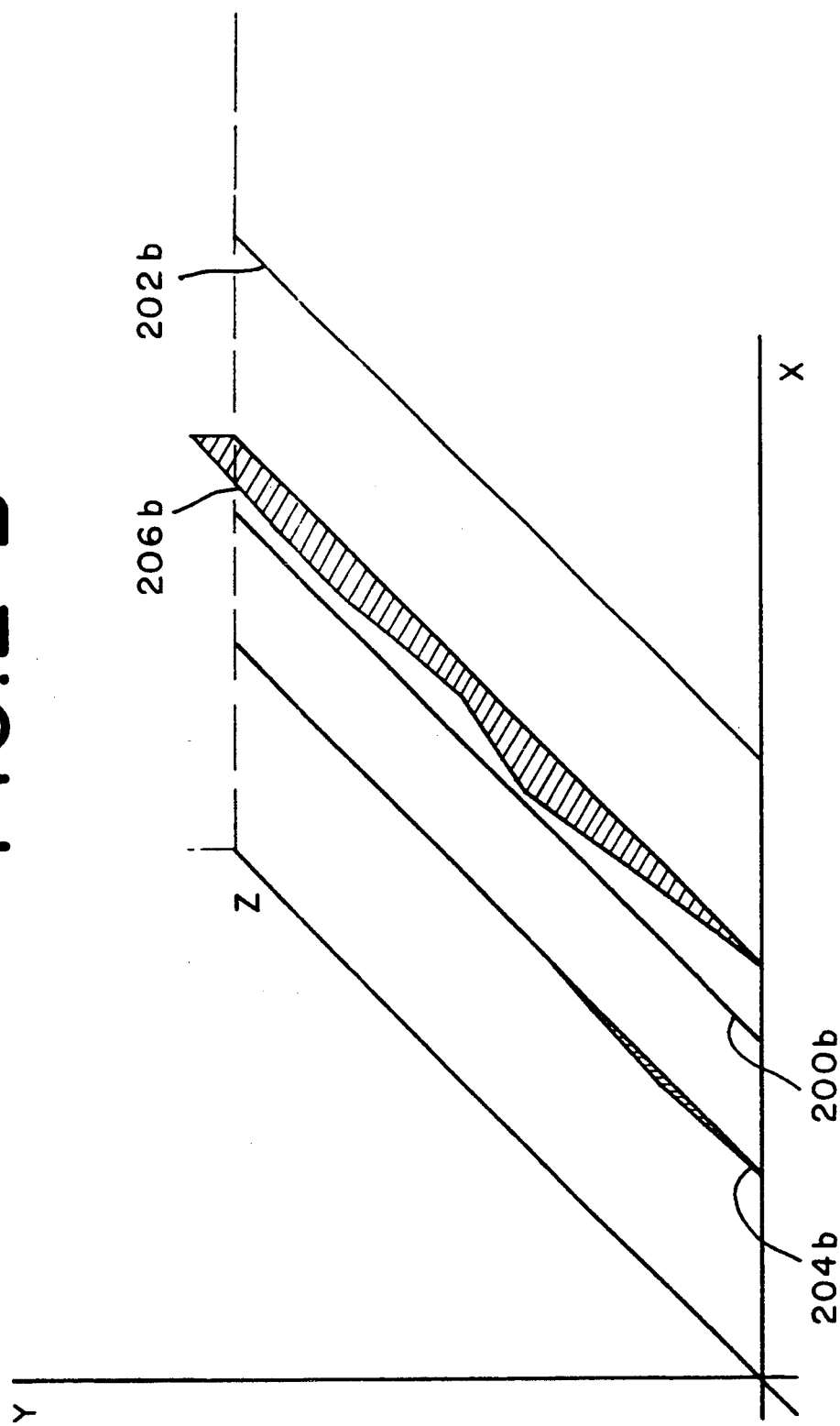
FIG. 2-B

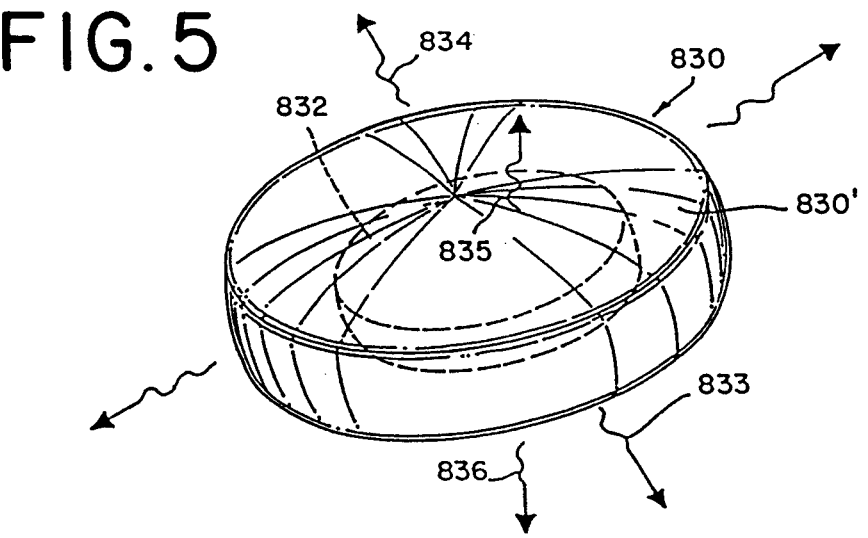
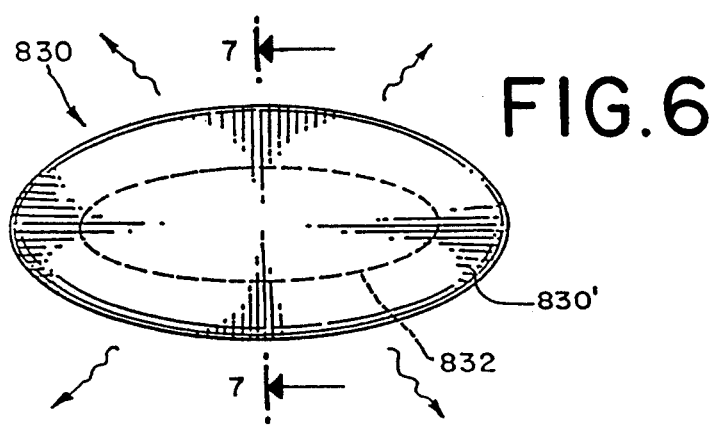
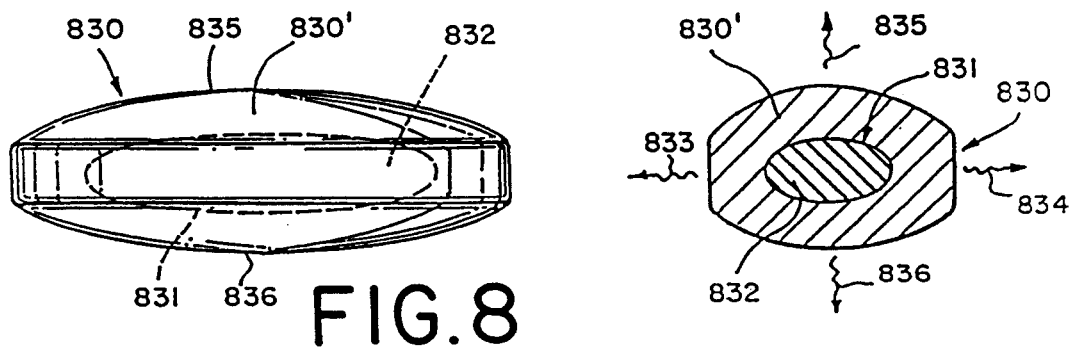

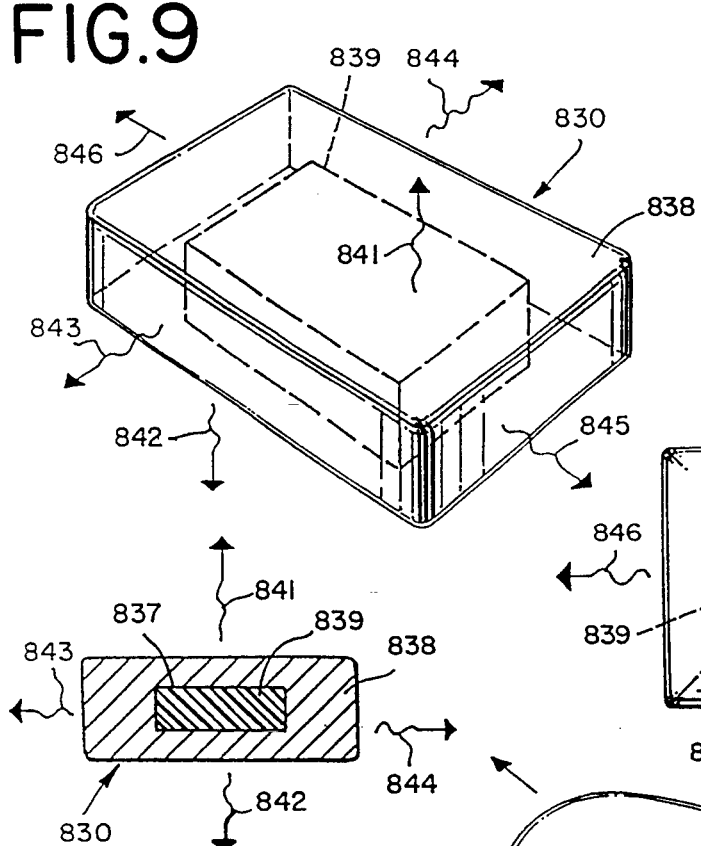
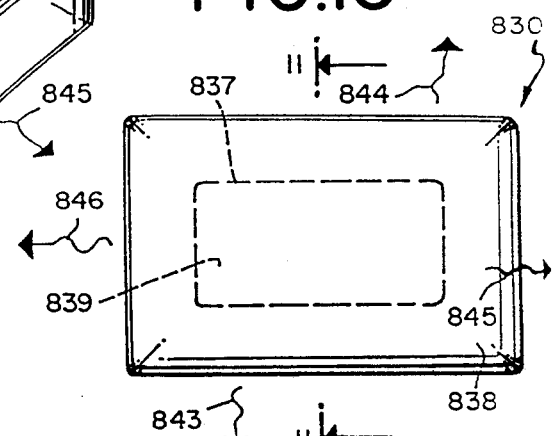
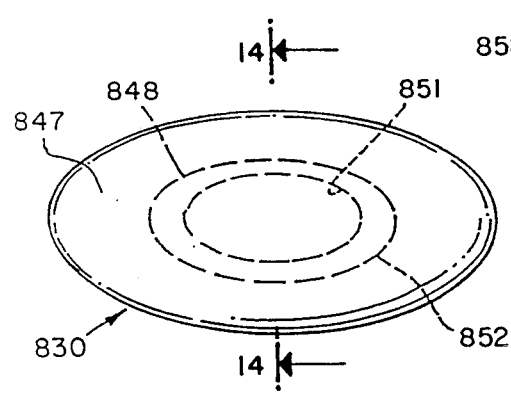
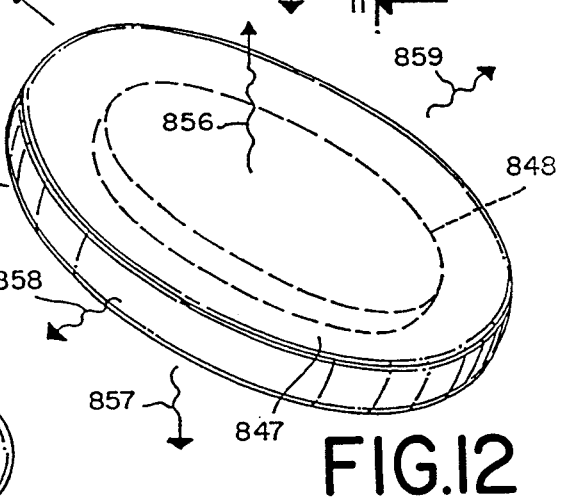
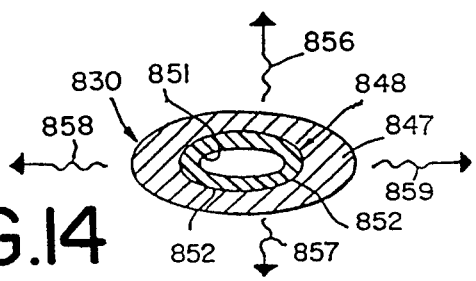

METHOD FOR REPELLING *AEDES AEGYPTAE* USING OXY-SUBSTITUTED CARBOCYCLIC COMPOUNDS

BACKGROUND OF THE INVENTION

This invention relates to the use of the cyclohexanol derivative having the structure:

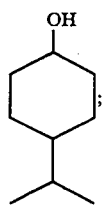

the lactone derivative having the structure:

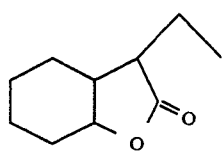

and
the phenyl derivative having the structure:

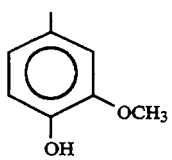

taken alone or in combination as repellents against the mosquito species, *Aedes aegyptae*.

A continuing need exists in the environment for repelling the mosquito species, *Aedes aegyptae*, from the proximity of mammalian species particularly in view of the fact that such insect species carry and transmit various diseases such as equine encephalitus.

A number of materials are well known in the art for repelling *Aedes aegyptae* including DEET ®. However, a need also arises for a repellent against *Aedes aegyptae* which is not only efficacious but is also aesthetically pleasing as an aroma.

The compounds having the structures:

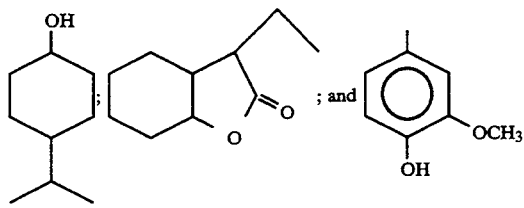

are efficacious *Aedes aegyptae* repellents, taken alone or taken in combination with one another, and at the same time they have aesthetically pleasing aromas. Nothing in the prior art implies that compounds having such structures have the unobvious, advantageous, effectiveness against *Aedes aegyptae* that the compounds of our invention have.

BRIEF DESCRIPTION OF THE DRAWINGS

FIG. 1A is a series of graphs depicted in three dimensions (in a rectangular mode for the "x" and "y" axes) showing the relative attractiveness or repellency for mosquitoes (*Aedes aegyptae*) of the compositions of matter:

(i) air;
(ii) the compound having the structure:

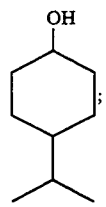

(iii) the compound having the structure:

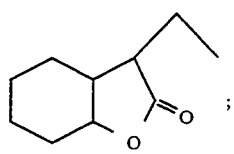

and
(iv) the compound having the structure:

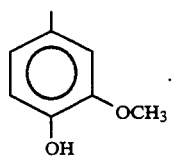

The graphs are based on experiments run for a total of one hour with six intervals of ten minutes each. The results are tabulated in Table I(A), infra.

FIG. 1B is a series of graphs depicted in three dimensions (in a rectangular mode for the "x" and "y" axes) showing the relative attractiveness or repellency for mosquitoes (*Aedes aegyptae*) of the compositions of matter:

(i) air;
(ii) the compound having the structure:

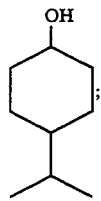

(iii) the compound having the structure:

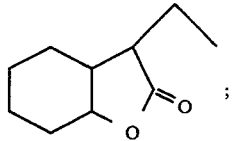

and
(iv) the compound having the structure:

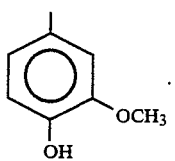

The graphs are based on experiments run for a total of 6 hours with six intervals of 1 hour each. The results are tabulated in Table I(B), infra.

FIG. 2A is a series of graphs depicted in three dimensions (in a rectangular mode for the "x" and "y" axes) showing the relative attractiveness or repellency for mosquitoes (*Aedes aegyptae*) of the compositions of matter:

(i) air;
(ii) the compound having the structure:

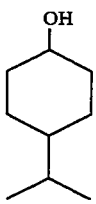

(iii) the compound having the structure:

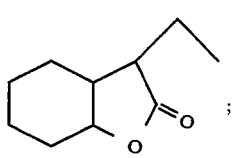

and
(iv) the compound having the structure:

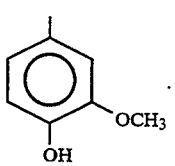

The graphs are based on experiments run for a total of 1 hour with six intervals of 10 minutes each. The results are tabulated in Table II (A), infra.

FIG. 2B is a series of graphs depicted in three dimensions (in a rectangular mode for the "x" and "y" axes) showing the relative attractiveness or repellency for mosquitoes (*Aedes aegyptae*) of the compositions of matter:

(i) air;
(ii) the compound having the structure:

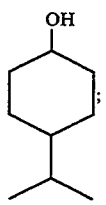

(iii) the compound having the structure:

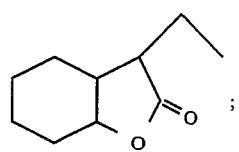

and
(iv) the compound having the structure:

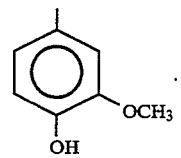

The graphs are based on experiments run for a total of 6 hours with six intervals of 1 hour each. The results are tabulated in Table II(B), infra.

Figure 3:
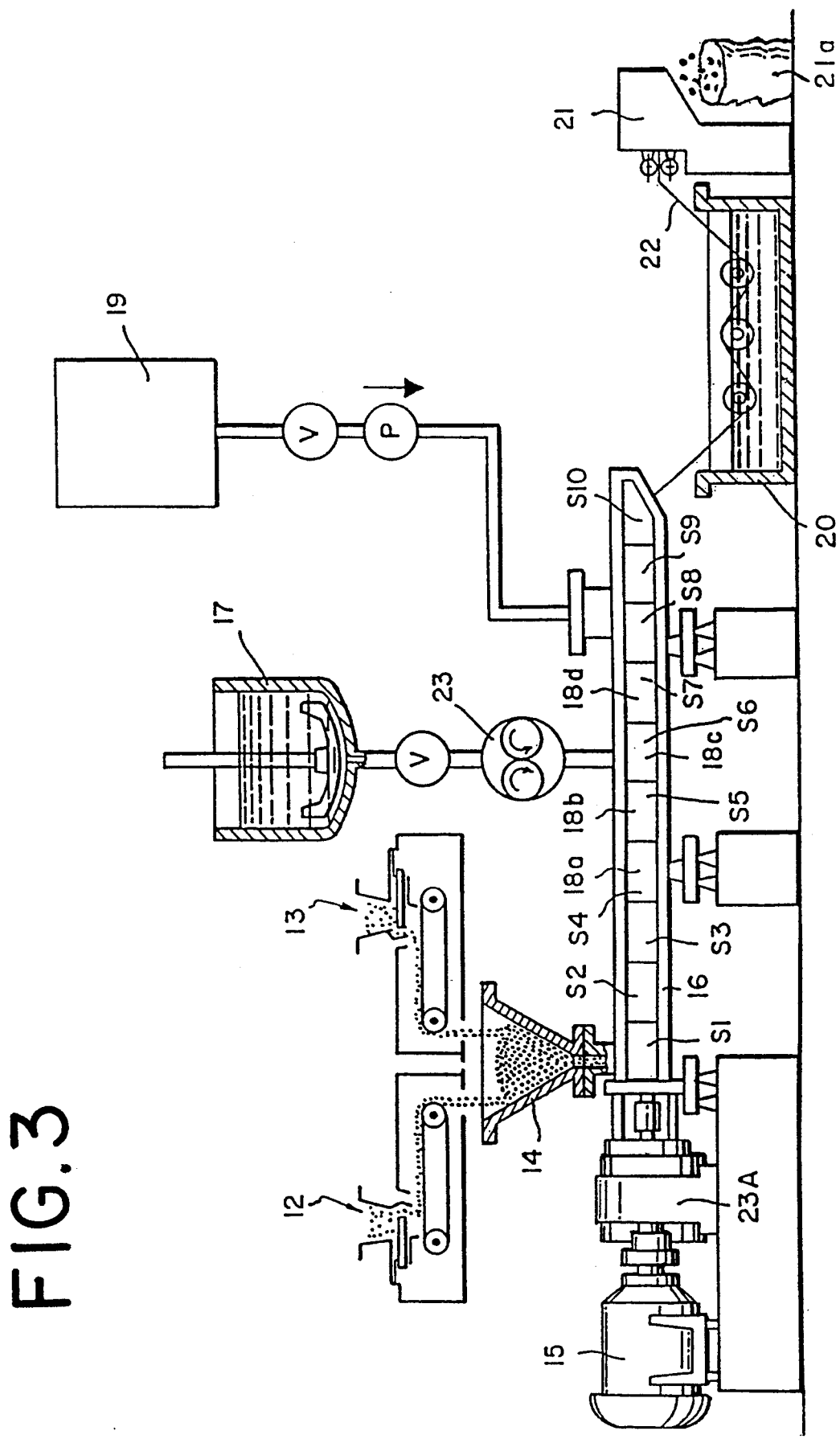

FIG. 3 is a cut-away side elevation schematic diagram of a screw extruder during the compounding of a resin with insect repellents including the oxy-substituted carbocyclic compounds of our invention, while simultaneously adding foaming agent into the hollow portion of the barrel of the extruder, and incorporates the pelletizing apparatus used in the pelletizing of the extruded foamed tow product produced as a result of the extrusion operation.

Figure 4:
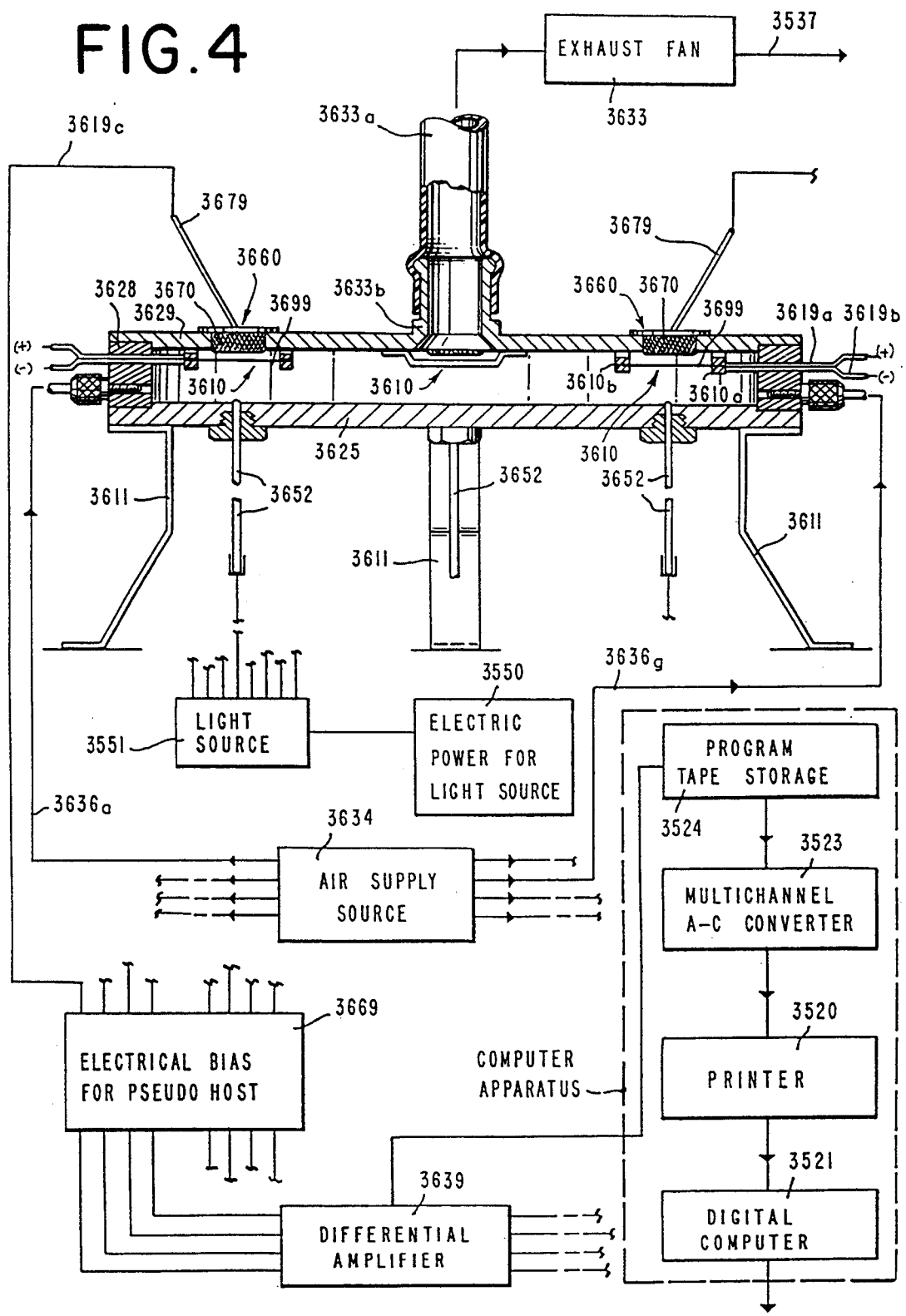

FIG. 4 is a cut-away side elevation view of the base section of the olfactometer apparatus of U.S. Letters Pat. No. 5,134,892 the specification for which is incorporated by reference herein, used in carrying out the testing of the repellents of our invention indicating in schematic block flow diagram form the utilization of computer-assisted efficacy measuring apparatus; but showing only an air supply entry into the side ports of the olfactometer apparatus with the treatment agent being contained in a control release matrix upstream from the air supply source.

FIG. 5 is a perspective view of an ellipsoidally shaped detergent tablet containing a solid core which includes fused foamed polymeric particles which contain insect repellents which are at least one of the oxy-substituted carbocyclic compounds of our invention and, if desired, also containing an additional polymer, e.g., polyethylene. The polymer particles may, if desired, also contain additional aromatizing agents.

FIG. 6 is the top view of the ellipsoidally-shaped detergent tablet of FIG. 5.

FIG. 7 is a cut-away front view of the ellipsoidally-shaped detergent tablet of FIG. 5 in the direction of the arrows in FIG. 6.

FIG. 8 is a side-view of the ellipsoidally-shaped detergent tablet of FIG. 5.

FIG. 9 is a perspective view of a rectangular parallelepiped-shaped detergent tablet containing a rectangular parallelepiped-shaped core comprising a major proportion of fused foamed polymeric particles which contain insect repellents (e.g., at least one of the oxy-substituted carbocyclic compounds our invention) and may or may not be additionally aromatized and, if desired, an additional polymer which may or may not contain insect repellent compositions and which may or may not be additionally aromatized.

FIG. 10 is a top view of the rectangular parallelepiped-shaped detergent tablet of FIG. 9.

FIG. 11 is a cut-away front view of the rectangular parallelepiped-shaped tablet of FIG. 9 looking in the direction of the arrows in FIG. 10.

FIG. 12 is a perspective view of an ellipsoidally-shaped detergent tablet containing a hollow insect repellent agent (and if desired, an additional aromatizing agent) containing core which includes fused foamed polymeric particles containing insect repellent and if desired, additional aromatizing agent or, in the alternative, a hollow core of fused foamed polymer wherein the insect repellent which is also an aroma imparting agent (and if desired, an additional aroma imparting agent) is in the solid polymer and not in the void of the plastic core.

FIG. 13 is a top view of the ellipsoidally-shaped detergent tablet of FIG. 12.

FIG. 14 is a front cut-away view of the ellipsoidally-shaped detergent tablet of FIG. 12 looking in the direction of the arrows in FIG. 13, the core thereof being hollow and either containing an insect repellent material of our invention (and if desired, an additional aroma imparting liquid) or in the alternative being a hollow core wherein the insect repellent material of our invention (and if desired, the additional aroma imparting material) is in the solid fused foamed polymeric particles which make up the core and wherein the void does not contain anything.

THE INVENTION

The instant invention applies to the uses of the compounds having the structures:

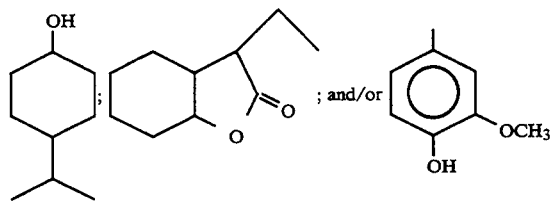

as repellents against the mosquito species, *Aedes aegyptae.*

Our invention is also related to the use of the foregoing insect repellent compositions of matter in personal soap compositions, for example, the insect repellent soap composition described in U.S. Pat. No. 4,707,496 issued on Nov. 17, 1987, the specification for which is incorporated by reference herein. Thus, in applying the teachings of U.S. Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 to 7% by weight of a soap of caprylic acid, from 3.8 to 7% of a soap of capric acid, from 32.1 to 45% of a soap of lauric acid, from 12 to 17.5% by weight of a soap of myristic acid, from 5.0 up to 10% by weight of a soap of palmitic acid, from 1.6 to 3% by weight of a soap of stearic acid, from 3.5 to 5% by weight of a soap of oleic acid and from 0.9 to 5% by weight of a soap of linoleic acid;

(ii) from 0.1 up to 2% by weight of C8–C18 straight chain fatty acids;

(iii) from 10 up to 30% by weight of at least one of the repellent chemicals of our invention, e.g., the compound having the structure:

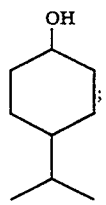

and/or the compound having the structure:

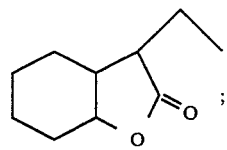

and/or the compound having the structure:

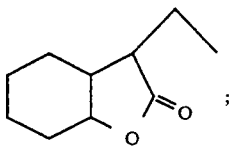

and/or the compound having the structure:

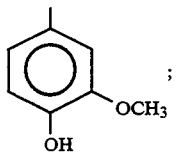

and (iv) from 0.2 up to 5% by weight of an effective residual insecticide as described in U.S. Pat. No. 4,707,496.

Other insect repellent soaps can be produced by adding one or more of the compounds having the structures:

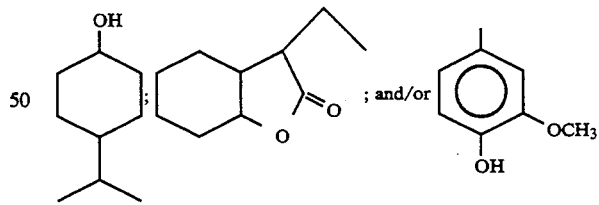

of our invention to one or more of the compositions described and claimed in U.S. Pat. No. 4,453,909 issued on Jun. 12, 1984 and U.S. Pat. No. 4,438,010 the specifications for which are incorporated by reference herein. Described in said U.S. Pat. No. 4,453,909 and U.S. Pat. No. 4,438,010 is a process for making a tablet of soap containing a perfume containing core, hollow, or solid, fabricated from a hard plastic material either thermosetting or thermoplastic. The soap from the resulting composite tablet is useable until the core is washed clean and contains functional ingredients, e.g., the repellents described, supra, having the structures:

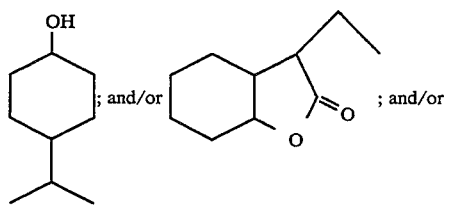 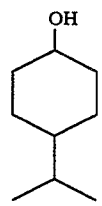

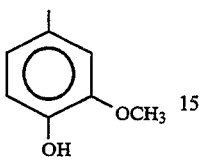

and optionally one or more additional aromatizing agents (in addition to the repellents described above) until the core is washed clean. This obviates the wastage of soap which normally occurs as a conventional soap tablet becomes very thin on use and at the same time gives rise to a continuously functional ingredient-containing soap (e.g., repellent and aromatizing) tablet. Thus, this invention also relates to detergent bars having a plastic core containing one or more of the above described compounds having the structures:

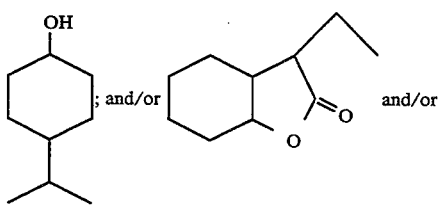

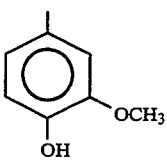

and optionally an additional perfuming material. More particularly, this invention relates to detergent bars intended for conventional toilet soap uses either as hand soaps or bath or shower soaps which are elastic or inelastic in nature but which contain a solid plastic core containing insect repellent and optionally perfume giving them unique properties which alleviate wastage thereof and causes the environment surrounding the soap on use thereof by an individual carrying out a washing procedure to be both insect repellent and aromatized in an aesthetically pleasing manner.

In addition, the compositions useful in repelling the Aedes aegyptae of our invention can also contain 1-nonen-3-ol described and claimed in U.S. Pat. No. 4,693,890 and 4,759,228 issued on Jul. 26, 1988, the specifications for which are incorporated by reference herein. The ratio of 1-nonen-3-ol:compound having the structure:

and/or the compound having the structure:

and/or the compound having the structure:

or each of the compounds of our invention in admixture useful in repellent compositions may vary from about 1 part 1-nonen-3-ol:99 parts oxy-substituted carbocyclic compound of our invention down to 99 parts 1-nonen-3-ol:1 part oxy-substituted carbocyclic compound of our invention.

In addition to the soap fabrication, another aspect of our invention relates to the formation of repelling articles (that is, articles having the ability to repel Aedes aegyptae from a member of the mammalian species such as a person) containing one or more of the compounds of our invention having the structures:

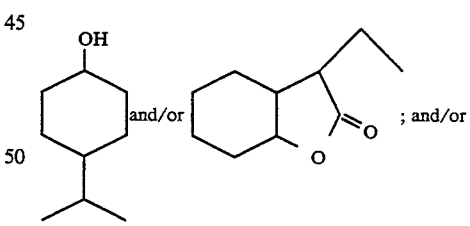

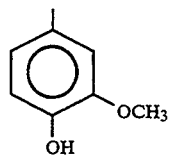

that is, articles useful for repelling the mosquito species Aedes aegyptae, in combination with compatible polymers (e.g., high density polyethylene or low density polyethylene). Thus, another aspect of our invention provides a process for forming polymeric particles containing at least one of the compounds having the structures:

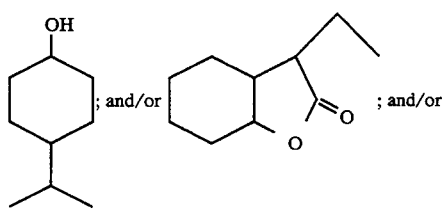
; and/or
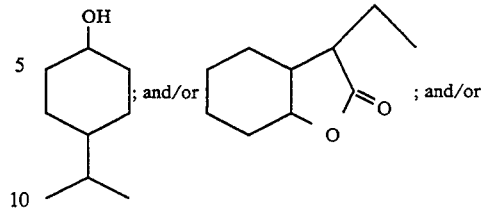
; and/or

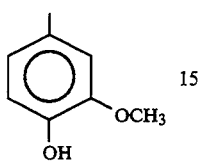

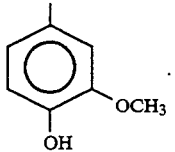

such as foamed polymeric particles which include a relatively high concentration of at least one of the compounds having the structures:

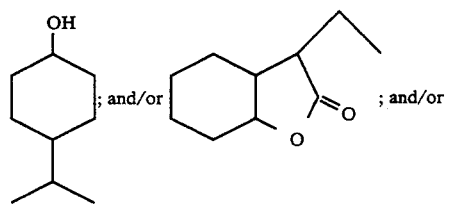
; and/or

Thus, another aspect of our invention relates to the formation of polymeric pellets containing at least one of the compounds having the structure:

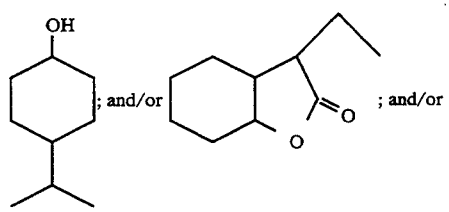
; and/or

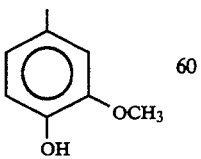

by means of introduction into a single screw or twin screw extruder of a polymer followed by at least one of the compounds having the structure:

In turn, the introduction of such an oxy-substituted carbocyclic compound of our invention may optionally be followed by introduction of a gaseous blowing agent or blowing agent which will produce a gas which is inert to the polymer and to the nitrile or alcohol of our invention previously introduced into the extruder.

The advantages of using a foamed polymeric particle and the details concerning the specific extruder and specific polymers so used are set forth at columns 30, 31, 32 and 33 of U.S. Letters Pat. No. 5,165,926 issued on Nov. 24, 1992 the specification for which is incorporated by reference herein.

The feed rate range of the insect repellent composition containing at least one of the oxy-substituted carbocyclic compounds of our invention may be between about 0.5% up to about 45% by weight of the polymer.

In addition, our invention relates to candle body materials which on use are both insect repellent and perfuming which contain one or more of the oxy-substituted carbocyclic compounds of our invention in order to repel the mosquito species, *Aedes aegyptae*. The details concerning the formation of such candle compositions are set forth at columns 34, 35 and 36 of U.S. Letters Pat. No. 5,165,926 issued on Nov. 24, 1992, the specification for which is incorporated by reference herein.

Specifically, the candle base composition can be standard paraffin wax or it can be transparent or pastel shaded as more particularly described in U.S. Letters Pat. No. 3,615,289 issued on Oct. 26, 1971 the disclosure of which is incorporated by reference herein and wherein the candle body comprises:

(i) a thermoplastic polyamide resin formed from linoleic acid polymerized with a polyamine compound;

(ii) an alkanol amide or alkanol amine; and (iii) a stearic acid compound. The percentage of insect repellent-perfumant of our invention in the candle body may vary from about 0.8% up to about 10% with a range of from about 0.8% up to about 2.0% being preferred when no additional perfume oil is used beyond the compounds having the structures:

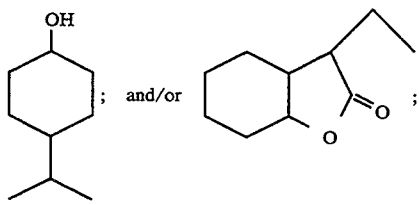

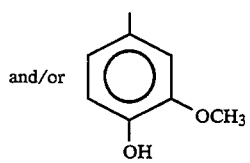

and with a range of from about 1.5% up to about 10% by weight of the overall composition being preferred when an additional perfume oil is used in conjunction with the compounds having the structures:

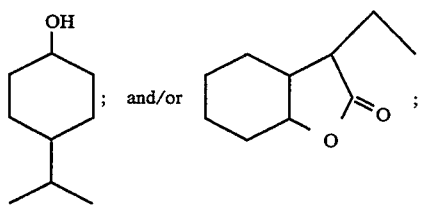

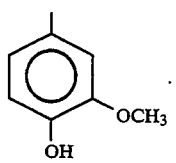

Specifically, the polyamide may be a "VERSAMID ®" resin which is a thermoplastic condensation product of polymerized linoleic acid with various polyamine compounds such as ethylene diamine, ethylene triamine and the like. Specific "VERSAMID ®" compounds are "VERSAMID ®900", "VERSAMID ®930", "VERSAMID ®940", "VERSAMID ®948", "VERSAMID ®950 and "VERSAMID ®1635". These compounds are products of the Henkel Chemical Corporation of Minneapolis, Minn. and the trademarks are owned by the Henkel Chemical Corporation of Minneapolis, Minn.).

Another substance useable in the clear candle composition consists of about 20–55% by weight of an alkanol amine or alkanol amide prepared by the reaction of a fatty acid ester and amine whereby the ester and the amine are in substantially equal proportions, for example, compounds such as BARLOL ®-12C2 (manufactured by the Barrid Chemical Company; the trademark BARLOL ® being owned by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready compounding of the insect repellent/perfume compositions of our invention up to a level of approximately 5% (total proportion of perfume oil-insect repellent composition). They are carriers for the perfumant-insect repellent and may be used in a proportion of between 1–50% by weight of the composition although the preferable range is between 20 to 30%. In this connection it is possible to use up to about 10% by weight of a perfumant/insect repellent if part of the formula is replaced by the material "NEVEX ®100", a product which is a coumarin-indene copolymer resin of very little unsaturation manufactured by the Neville Chemical Company (the trademark NEVEX ® being owned by the Neville Chemical Company).

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by reference herein. Such compositions of matter include:

(a) from about 35% up to about 85% by weight of an oil which is normally liquid at room temperature, chosen from the group consisting of light mineral oils and natural oils having iodine values substantially within the range of 40–135;

(b) from about 7% up to about 40% by weight of a long chain polyamide having a molecular weight substantially within the range of 6000–9000 and a softening point substantially within the range of 18° C.-48° C.; and (c) from about 7% up to about 30% of an alcohol selected from the group consisting of 8 to 12 carbon primary alcohols.

DETAILED DESCRIPTION OF THE DRAWINGS

FIG. 1A is a series of graphs depicted in three dimensions (in a rectangular mode for the "x" and "y" axes) showing the relative attractiveness or repellency of the following compositions of matter:

(i) air;

(ii) the compound having the structure:

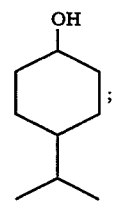

(iii) the compound having the structure:

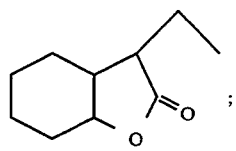

and (iv) the compound having the structure:

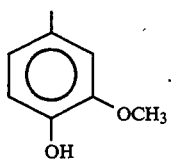

The graph indicated by reference numeral 100a is for the compound having the structure:

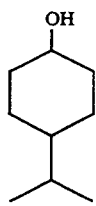

The graph indicated by reference numeral 102a is for the compound having the structure:

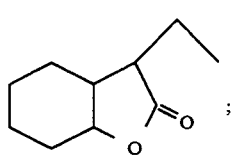

the graph indicated by reference numeral 104a is for the compound having the structure:

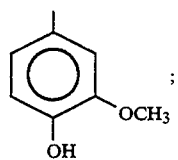

the graph indicated by reference numeral 106a is for air.

The graphs show the attractancy or repellency for mosquitoes (*Aedes aegyptae*) using the apparatus of FIG. 4. The graphs are based on experiments run for a total of 1 hour with six intervals of 10 minutes each. The graphs are tabulated in Table I(A) as follows:

TABLE I(A)

| Composition Tested | Graph No. | Insects Collected Per Interval | | | | | |
|---|---|---|---|---|---|---|---|
| The compound having the structure: [cyclohexanol with isopropyl] | 100a | 4 | 0 | 2 | 0 | 0 | 0 |
| The compound having the structure: [bicyclic lactone with ethyl] | 102a | 1 | 0 | 0 | 0 | 0 | 0 |
| The compound having the structure: [methyl-methoxyphenol] | 104a | 1 | 0 | 0 | 0 | 0 | 0 |
| Air | 106a | 168 | 378 | 259 | 245 | 239 | 272 |

FIG. 1B is a series of graphs depicted in three dimensions (in a rectangular mode for the "x" and "y" axes) showing the relative attractiveness or repellency for or against the mosquito species, *Aedes aegyptae*, of the following compositions of matter:

(i) air;
(ii) the compound having the structure:

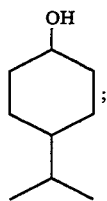

(iii) the compound having the structure:

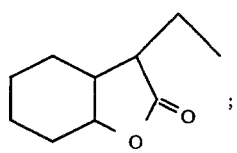

and (iv) the compound having the structure:

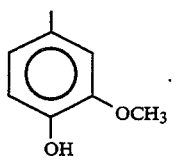

The graph indicated by reference numeral 100b is for the compound having the structure:

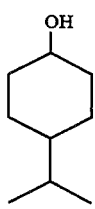

The graph indicated by reference numeral 102b is for the compound having the structure:

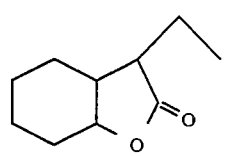

The graph indicated by reference numeral 104b is for the compound having the structure:

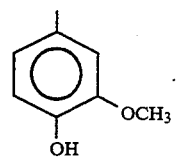

The graph indicated by reference numeral 106b is for air. The graphs show the attractancy or repellency for mosquitoes (*Aedes aegyptae*) using the apparatus of FIG. 4. The graphs are based on experiments run for a total of 6 hours with 6 intervals of 1 hour each. The results are tabulated in Table I(B) below:

TABLE I(B)

| Composition Tested | Graph No. | Insects Collected Per Interval | | | | | |
|---|---|---|---|---|---|---|---|
| The compound having the structure: (4-isopropylcyclohexanol) | 100b | 0 | 0 | 3 | 38 | 65 | 85 |
| The compound having the structure: (ethyl-substituted bicyclic lactone) | 102b | 1 | 2 | 5 | 3 | 3 | 13 |
| The compound having the structure: (iodo-methoxyphenol) | 104b | 0 | 0 | 0 | 0 | 0 | 4 |
| Air | 106b | 272 | 241 | 430 | 380 | 460 | 481 |

FIG. 2A is a series of graphs depicted in three dimensions (in a rectangular mode for the "x" and "y" axes) showing the relative attractiveness or repellency of the following compositions of matter:
(i) air;
(ii) the compound having the structure:

(iii) the compound having the structure:

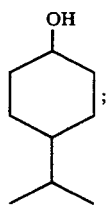

and (iv) the compound having the structure:

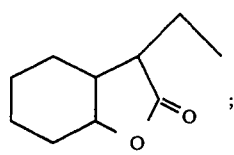

The graph indicated by reference numeral 200a is for the compound having the structure:

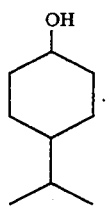

The graph indicated by reference numeral 202a is for the compound having the structure:

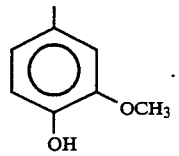

The graph indicated by reference numeral 204a is for the compound having the structure:

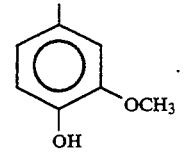

The graph indicated by reference numeral 206a is for air. The graphs show the attractancy or repellency for the mosquito species, *Aedes aegyptae*, using the apparatus of FIG. 4. The graphs are based on experiments run for a total of 1 hour with six intervals of 10 minutes each. The results are tabulated in Table II(A) as follows:

TABLE II(A)

| Composition Tested | Graph No. | Insects Collected Per Interval | | | | | |
|---|---|---|---|---|---|---|---|
| The compound having the structure:<br>(4-isopropylcyclohexanol) | 200a | 0 | 0 | 0 | 0 | 0 | 0 |
| The compound having the structure:<br>(ethyl hexahydrobenzofuranone) | 202a | 2 | 0 | 0 | 6 | 1 | 0 |
| The compound having the structure:<br>(methoxyphenol) | 204a | 1 | 0 | 0 | 0 | 3 | 17 |
| Air | 206a | 101 | 53 | 162 | 7 | 65 | 66 |

FIG. 2B is a series of graphs depicted in three dimensions (in a rectangular mode for the "x" and "y" axes) showing the relative attractiveness or repellency of the following compositions of matter:

(i) air;
(ii) the compound having the structure:

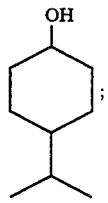

(iii) the compound having the structure:

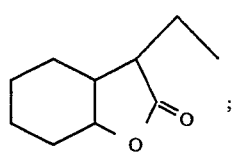

and
(iv) the compound having the structure:

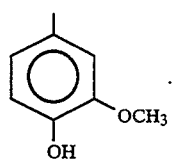

The graph indicated by reference numeral 200b is for the compound having the structure:

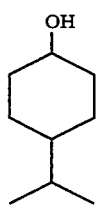

The graph indicated by reference numeral 202b is for the compound having the structure:

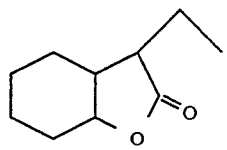

The graph indicated by reference numeral 204b is for the compound having the structure:

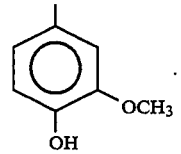

The graph indicated by reference numeral 206b is for air. The graphs show the attractancy or repellency for mosquitoes (*Aedes aegyptae*) using the apparatus of FIG. 4. The graphs are based on experiments run for a total of six hours with six intervals of one hour each. The results are tabulated in Table II(B) below:

TABLE II(B)

| Composition Tested | Graph No. | Insects Collected Per Interval | | | | | |
|---|---|---|---|---|---|---|---|
| The compound having the structure: | 200b | 0 | 0 | 0 | 0 | 1 | 4 |
| The compound having the structure: | 202b | 0 | 4 | 7 | 0 | 0 | 3 |
| The compound having the structure: | 204b | 17 | 10 | 9 | 2 | 5 | 3 |
| Air | 206b | 66 | 114 | 62 | 99 | 90 | 69 |

In referring to the extruder of FIG. 3, polymer 12 and 13 is admixed in vessel 14 and added at barrel segment S-1 of barrel 16 to the extruder which is powered by motor 15, held in place by bracket 23A. Simultaneously into barrel segment S-6 (one of segments 18a, 18b, 18c or 18d) is added the insect repellent composition which is one or more of the oxy-substituted carbocyclic compounds of our invention previously held in container 17. The repellent/perfumant mixture is pumped through pump 23 into barrel segment 18c/S-6. Simultaneously, foaming agent is added from vessel 19 into barrel segment S-8. From barrel segment S-10, a foamed tow containing polymer having imbedded therein insect repellent/perfume is passed through cooling bath 20 and the cooled tow 22 is then passed into macerating machine 21 wherein the tow is chopped into particles and held in container 21a for future use, e.g., for use in conjunction with the manufacture of insect repellent soap or detergent bars described in detail, infra.

Referring to FIGS. 5–14, inclusive, a preferred embodiment of our invention comprises an ellipsoidally shaped detergent tablet 830. A preferred embodiment of our invention comprises an ellipsoidally-shaped detergent tablet 830 containing a solid plastic core 832 which can be fabricated from, for example, polyethylene, polypropylene, nylon, a biodegradable polymer such as poly(epsilon caprolactone) or any polymer capable of having therein microvoids from which an insect repelling/perfuming substance, e.g., at least one of the oxy-substituted carbocyclic compounds of our invention will be controllably transported from the plastic core into and through the soap cake over a reasonable period of time during the use of the soap cake. Such polymers can be microporous polymers, such as those described in U.S. Letters Pat. No. 4,247,498 issued on Jan. 27, 1981, the specification for which is incorporated herein by reference. Surrounding the central plastic core containing insect repellent 832, is detergent 830' which is in the solid phase at ambient conditions, e.g., room temperature and atmospheric pressure. Examples of workable detergents 830' are "elastic" detergents such as those described in U.S. Letters Pat. No. 4,181,632 issued on Jan. 1, 1980, the disclosure of which is incorporated herein by reference, or "transparent" soaps such as those set forth in U.S. Letters Pat. No. 4,165,293 issued on Aug. 21, 1979, the disclosure of which is incorporated herein by reference. Other examples of the detergent 830' useful in our invention are those set forth as "variegated soaps" in Canadian Letters Patent No. 1,101,165 issued on May 19, 1981.

On use of the soap tablet 830 or detergent bar, the insect repellent agent originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelepiped tablet as is shown in FIGS. 9, 10 and 11 containing solid plastic core 839. The insect repellent located in solid plastic core 839 on use of the detergent bar passes through at steady state, surface 837 of FIG. 10, detergent 838 and finally surface 839 at, for example, locations 840, 841, 842 and 843. The environment surrounding the detergent bar on use thereof is then treated with the insect repellent (that is, at least one of the oxy-substituted carbocyclic compounds of our invention) at 843, 844 and 845, for example. Optionally, additional aromatizing agent can also be contained in the detergent bar (if desired) and so the environment surrounding the detergent bar on use thereof would also be aesthetically aromatized at 843, 844 and 845, for example, if the appropriate oxy-substituted carbocyclic compound of our invention is insufficient for such aromatization. In certain instances such appropriate oxy-substituted carbocyclic compounds of our invention are indeed sufficient for such aromatization.

As is shown in FIGS. 12, 13 and 14, the plastic core of the detergent tablet 830 may have a single finite void at its center 851 (of FIGS. 13 and 14) in which the insect repellent agent and, optionally, any additional aromatizing agents are contained. The plastic core is a shell 848 having outer surface 852 (shown in FIGS. 13 and 14). The insect repellent agent (and, optionally, any additional aromatizing agent) contained in the void in the plastic core permeates through shell 848, past surface 852 at a steady state, through the detergent 847 and to the environment at, for example, 856, 857 858 and 859.

In addition to the insect repellent contained in the core, e.g., core 839 or core void, the core can also contain other materials for therapeutic use, for example, bacteriastats, deodorizing agents and the like which are compatible with the appropriate oxy-substituted carbocyclic compound-containing compositions of our invention. In the alternative, the plastic core of the detergent tablet of FIGS. 12, 13 and 14 may have an empty single finite void at its center 851 with the insect repellent contained in the shell 848.

At the end of the use of the detergent tablet, the hollow core or the solid core can be used as an insect repelling and aroma imparting or air freshener household article. In addition, depending on the ratio of the volume of the void 851, to the solid part of the detergent tablet of FIGS. 12, 13 and 14, the detergent tablet of FIGS. 12, 13 and 14 can be so fabricated that it will float on the surface of the liquid in which it is being used and this physical attribute has certain obvious advantages.

The data set forth in FIGS. 1A, 1B, 2A and 2B were determined using the olfactometer of FIG. 4.

Referring to the olfactometer of FIG. 4, said olfactometer is described in detail in U.S. Letters Pat. No. 5,118,711 issued on Jun. 2, 1992, the specification for which is incorporated by reference herein.

Referring to FIG. 4, air supply source 3634 provides air to mixing station 3636 wherein the air is mixed with treatment agent from treatment agent source 3635 (source of, for example, the repellent composition which is an appropriate oxy-substituted carbocyclic compound of our invention). The resulting mixture passes through tube 3636g and enters the apparatus through the side portals. The entry is through a spacer plate above base plate 3625. The entry of the air-treatment agent is in a direction parallel to the surface of base plate 3625. Thus, the base plate 3625 is separated from spacer plate 3629 for the air-treatment agent (e.g., at least one of the oxy-substituted carbocyclic compounds of our invention).

Air exits through line 3633a using exhaust fan 3633. The air exit is indicated by reference numeral 3537.

Simultaneously, with the supplying of air and treatment agent from mixing station 3636, light is supplied from beneath the enclosed insect feeding and/or stimulating means through light guides 3652, from light source 3551 which is powered by electric power supply 3550 marketed by RADIO SHACK ® Division of Tandy Corporation of Fort Worth, Tex. 76102 under the trademark ARCHER ®, Catalog No. 276-228 ("1.0 mm optical plastic fiber length 5 meter"). An example of light source 3551 is KRATOS Monochromatic Illuminator GM 100 Miniature VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source from location 3634 and treatment agent from location 3635 is mixed at mixing station 3636 whereupon treatment agent and air in admixture is passed through lines 3636a and 3636g through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628. It should be noted that the spacer plate 3629, spacer ring 3628 and base plate 3625 enclose the entire "enclosed insect feeding and/or stimulating means" which have controlled limited access to the external environment surrounding the apparatus and in which the insects are to be tested, e.g., Aedes aegyptae species of mosquitoes, or are placed.

The insect attractant quantitative detecting means made up of wires 3699 (the entire grid being denoted using reference numeral 3610) is located immediately beneath the porous membrane 3670, the outer surface of which contains a feeding stimulant composition or stimulant composition for insects (for example, agar). Immersed in the feeding stimulant composition or stimulant composition for insects (e.g., agar) is electrode 3679 connected to wire 3619 which connects with either wire 3619a or 3619b which is connected to the grid wires 3699 (which make up the insect attractant quantitative detecting means located immediately below lamina 3670).

As stated, supra, the sensor causes an electrical impulse caused by the pressure of the insect's landing to proceed through wires 3619a and 3619b to an electrically biased differential amplifier 3639 (using electrical power supply 3539) also connected to wire 3619c which is connected to the electrode 3679 which is immersed in the feeding stimulant composition or stimulant for the insect and then to a multi-channel A.C. converter 3523. Converter 3523 is associated with program tape storage 3524, printer 3520 and data link to digital computer 3521. Differential amplifer 3639 is connected in series to electrical bias for pseudo host 3669 which in turn is connected to wire 3619 which in turn is connected to the electrode 3679 immersed in the insect stimulant composition located on the surface of porous lamina 3670.

The mixture of oxy-substituted carbocyclic compounds of our invention operable in the context of our invention may vary from one part of the compound having the structure:

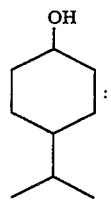

50 parts by weight of the compound having the structure:

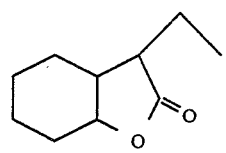

49 parts by weight of the compound having the structure:

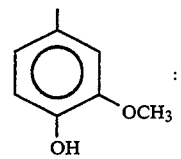

to one part by weight of the compound having the structure:

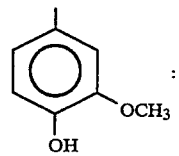

parts by weight of the compound having the structure:

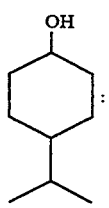

and 49 parts by weight of the compound having the structure:

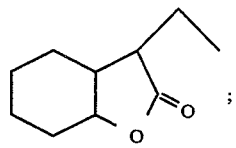

or may vary from one part by weight of the compound having the structure:

99 parts by weight of the compound having the structure:

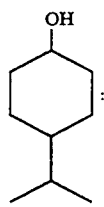

to 99 parts by weight of the compound having the structure:

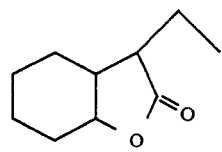

1 part by weight of the compound having the structure:

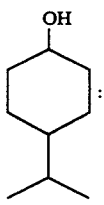

or may be from 1 part by weight of the compound having the structure:

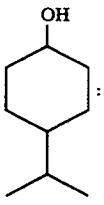

99 parts by weight of the compound having the structure:

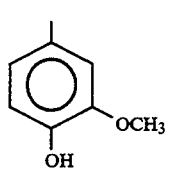

to 99 parts by weight of the compound having the structure:

1 part by weight of the compound having the structure:

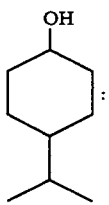

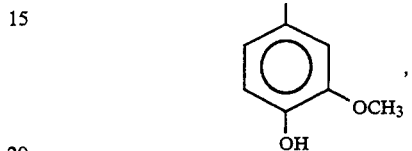

for example.

The following examples are illustrative and the instant patent application is intended to be restricted only to the scope of the claims and not to the examples.

All parts indicated are parts by weight unless otherwise specified.

EXAMPLE I

A transparent candle base mixture i s produced by intimately admixing the following ingredients:

| Ingredients | Parts by Weight |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® | 1.5 |
| Isopropyl Isostearate | 4.0 |
| Isopropyl Myristate | 4.0 |

The foregoing mixture is placed in an autoclave and intimately admixed with 22% by weight of the entire mixture of a perfuming-insect repellent composition containing the following ingredients:

| Ingredients | Parts by Weight |
|---|---|
| APO PATCHONE ™* having the structure: | 25 |

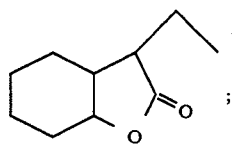

(*trademark of International Flavors & Fragrances Inc.)

| TONKA LACTONE ™* having the structure: | 50 |
|---|---|

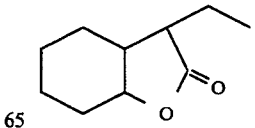

(*trademark of International Flavors & Fragrances Inc.).

| CREOSOL 340 ™* having the structure: | 25 |
|---|---|

-continued

| Ingredients | Parts by Weight |
|---|---|
| 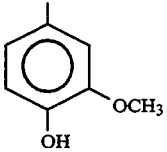 | |
| (*trademark of International Flavors & Fragrances Inc.). | |

The autoclave is sealed and heated to 180° C. under 25 atmospheres pressure and maintained with vigorous shaking for a period of five hours. At the end of the five hour period, the autoclave is depressurized (being under a nitrogen pressure atmosphere) and the autoclave is opened and the contents are then poured into cylindrical candle molds 4" in height and 2" in diameter containing 0.125" (diameter) wicks. The resulting candles have efficacious *Aedes aegyptae* repellency and have aesthetically pleasing aromas on use.

The candles are effective in preventing the mosquito species, *Aedes aegyptae*, from entering a room in which eight candles have been burning for 20 minutes, the said room having dimensions of 6'×15'×15' and having a 2'×2' open portal adjacent to a mosquito-infested region in the month of August, 1993 in the temperate zone of Highlands, N.J. adjacent Raritan Bay.

EXAMPLE II A study was conducted to evaluate the efficacy of candles which are designated as "A" "B" and "C" in repelling the mosquito species, *Aedes aegyptae*.

Candle "A" contained 95% Paraffin Wax and 5% of APO PATCHONE ™ having the structure:

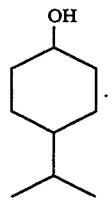

Candle "B" contained 90% Paraffin Wax and 10% citronella oil.

Candle "C" contained only Paraffin Wax.

The candles are allowed to burn for 20 minutes and the number of mosquitoes (*Aedes aegyptae*) repelled is recorded for the next 60 minutes with the following equipment and procedure:

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged grey mouse was used as an attractant and was placed inside the chamber in the larger section of the repellency cage.

Test Insects

*Aedes aegyptae* mosquitoes.

Procedure

For each replicate, 75 to 100 *Aedes aegyptae* mosquitoes were removed from the rearing cage by means of a vacuum aspirator, and transferred by carbon dioxide anesthesia to the inner cage containing the grey mouse. The assembled cage was placed in one of the upper ventilation ports of the chamber. For each experimental situation the test insects were transferred to a clean cage containing the mouse. A candle containing the insect repellent substance to be tested was placed centrally on the chamber floor and burned for 20 minutes before initiating the repellency counts. The maximum period for the repellency counts was 60 minutes. The first repellency count was made 10 minutes after the burning ended, and subsequent counts were taken at 5-minute intervals thereafter. The number of *Aedes aegyptae* mosquitoes repelled were those escaping to the outside cage. For the control, counts were made in a similar manner but no candle was burned.

The same three candles were used for all four replicates. Between replicates the chamber was exhausted, the Kraft paper flooring for the chamber was replaced, and the two screened repellency cages were submerged in hot detergent water, rinsed and dried.

Results

The overall average percent of *Aedes aegyptae* mosquitoes repelled for each candle for 60 minutes was as follows:

Candle "A" — 99%
Candle "B" — 51%
Candle "C" — 8%.

What is claimed is:

1. A method for repelling *Aedes aegyptae* consisting essentially of the step of exposing a three dimensional space inhabitable by *Aedes aegyptae* to an *Aedes aegyptae*-repelling effective concentration and quantity of the compound having the structure:

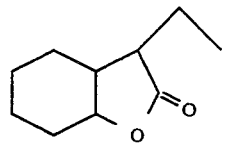

wherein said compound having the structure:

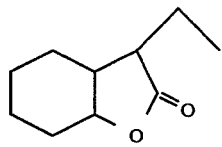

(a) is present in a microporous polymer at the level of from about 0.5% up to about 45% by weight of the polymer;

(b) is present in the candle body of a burning candle in an amount of from about 0.8% up to about 2.0%; or (c) is present in a soap being applied in use in an amount of from 10 up to 30% by weight of the soap.

2. The process of claim 1 wherein the compound having the structure:

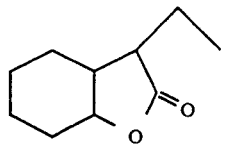

is present in a microporous polymer in an amount of from about 0.5% up to about 45% by weight of the polymer.

3. The process of claim 1 wherein the compound having the structure:

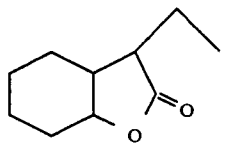

is present in a burning candle in an amount of from about 0.8% up to about 2.0% by weight of the candle composition.

4. The process of claim 1 wherein the compound having the structure:

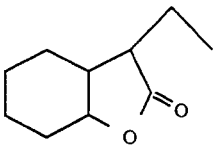

is present in a soap-in-use in an amount of from 10% up to 30% by weight of the soap-in-use.

5. The process of claim 2 wherein the compound having the structure:

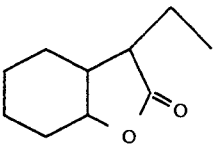

is imbedded in a polymer selected from the group consisting of copolymers of ethylene and a vinyl monomer selected from the group consisting of:
 (a) vinyl acetate;
 (b) ethyl acrylate;
 (c) methyl acrylate;
 (d) butyl acrylate; and
 acrylic acid and the hydrolyzed copolymer of ethylene and vinyl acetate compatible with the compound having the structure:

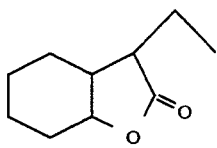

* * * * *